United States Patent
Dubois et al.

(10) Patent No.: US 7,117,134 B2
(45) Date of Patent: Oct. 3, 2006

(54) METHOD TO OPTIMIZE GENERATION OF ULTRASOUND USING MATHEMATICAL MODELING FOR LASER ULTRASOUND INSPECTION

(75) Inventors: Marc Dubois, Clifton Park, NY (US); Peter W. Lorraine, Niskayuna, NY (US); Robert J. Filkins, Niskayuna, NY (US); Thomas E. Drake, Fort Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 757 days.

(21) Appl. No.: 09/982,688

(22) Filed: Oct. 18, 2001

(65) Prior Publication Data

US 2003/0078681 A1 Apr. 24, 2003

(51) Int. Cl.
*G06G 7/48* (2006.01)
(52) U.S. Cl. ............................................. 703/5; 73/632
(58) Field of Classification Search ............... 703/5; 73/632; 367/118, 124
See application file for complete search history.

(56) References Cited

U.S. PATENT DOCUMENTS

| | | | | |
|---|---|---|---|---|
| 3,675,190 A | * | 7/1972 | Auer et al. ............... | 367/93 |
| 3,715,672 A | * | 2/1973 | Suter ........................ | 327/73 |
| 4,228,688 A | | 10/1980 | Sharpe ..................... | 73/631 |
| 4,276,779 A | * | 7/1981 | Davis, Jr. ................. | 73/626 |
| 4,393,711 A | | 7/1983 | Lapides ................... | 73/592 |
| 4,440,173 A | * | 4/1984 | Hudziak et al. ........... | 607/30 |
| 4,520,670 A | | 6/1985 | Salomonsson et al. .... | 73/602 |
| 4,609,994 A | | 9/1986 | Bassim et al. ............. | 364/551 |
| 4,655,086 A | | 4/1987 | Mielnicka-Pate et al. ..... | 73/646 |
| 5,161,128 A | * | 11/1992 | Kenney .................... | 367/181 |
| 5,216,921 A | | 6/1993 | Tsuboi ...................... | 73/579 |
| 5,621,656 A | | 4/1997 | Langley .................... | 364/508 |
| 5,832,412 A | | 11/1998 | Guez ......................... | 702/75 |
| 5,883,309 A | | 3/1999 | Vossick et al. ............. | 73/602 |

FOREIGN PATENT DOCUMENTS

| | | |
|---|---|---|
| EP | 0346951 A2 | 12/1989 |
| EP | 0427320 A2 | 5/1991 |
| EP | 0377571 A1 | 12/1992 |
| EP | WO9739691 A1 | 8/1999 |
| EP | WO9739690 A1 | 2/2000 |

OTHER PUBLICATIONS

Harold Chestnut, Systems Engineering Tools, Wilson and Wilson, p. 437.*

* cited by examiner

*Primary Examiner*—Albert W. Paladini
(74) *Attorney, Agent, or Firm*—Koestner Bertani, LLP (57) ABSTRACT

The invention is directed to a laser ultrasound testing system with adaptive generation of sonic energy signals. The system may detect or test features of the manufactured object such as defects and layer properties. A laser generator initiates a sonic energy signal in a manufactured object. A measuring device measures the sonic energy signal. Then, a signal analyzer and/or a model processor determine if the signal is optimized. If the signal is not optimized, optimized operating characteristics of the laser generator are calculated. These optimized operating characteristics may include wavelength, beam dimension, temporal profile and power. Next, the laser generator initiates an improved sonic energy signal by utilizing the optimized operating characteristics. In this manner, more accurate testing and detection is achieved.

55 Claims, 9 Drawing Sheets

METHOD TO OPTIMIZE GENERATION OF ULTRASOUND USING MATHEMATICAL MODELING FOR LASER ULTRASOUND INSPECTION

BACKGROUND OF THE INVENTION

1. Field of the Invention

The present invention generally relates to an apparatus and method for improving ultrasonic signal generation by an ultrasonic testing device. In particular, the present invention relates to optimizing an ultrasonic response in a manufactured object or part by adaptively adjusting operating characteristics of a laser ultrasound testing device.

2. Description of Prior Art

Ultrasound testing methods are non-invasive, generally non-destructive, techniques used to measure features of materials. These features may include layer thickness, cracks, delamination, voids, disbonds, foreign inclusions, fiber fractions, fiber orientation and porosity. The features influence a given material's qualities and performance in given applications. Each application places unique demands on the material's qualities including the need for differing strength, flexibility, thermal properties, cost, or ultraviolet radiation resistance. With the changing demands, more non-invasive, non-destructive testing of materials is being performed using techniques such as ultrasound testing.

Ultrasound techniques are applied in research as well as industrial settings. In research, ultrasound techniques are used to test new materials for desired features. The techniques are also used to seek defects in material that has undergone stress or environmental endurance testing. In industry, the techniques are used during scheduled servicing to inspect parts for defects. Aircraft, automobile and other commercial industries have shown increasing interest in these techniques.

Ultrasound testing includes transducer-induced, laser, electromagnetic-induced and plasma-initiated ultrasound. Transducer-induced ultrasound techniques use piezoelectric transducers to induce an ultrasonic signal in an object.

Laser ultrasound techniques use a laser pulse. When the laser pulse is directed at an object, it causes thermal expansion in a small region. This thermal expansion causes ultrasonic waves. These ultrasonic waves are then measured by a detector and converted into information about the features of the object. The laser pulse may be generated by several lasers including a ruby laser, a carbon dioxide laser, and a Nd:YAG laser.

In some cases, a higher laser-energy density can be used and some matter at the material surface is ablated. The recoil effect of the pulverized matter launches ultrasonic waves in the material. Similarly to the thermoelastic regime, this ablation regime produces ultrasonic waves can be detected and converted into information about the features of the object.

The electromagnetic-induced ultrasound technique can be used on metallic parts. Coils in the transducer produce an electromagnetic field that induces ultrasonic waves in the sample.

Similar to the laser ultrasound, plasma-induced ultrasound techniques cause thermal expansion initiated ultrasonic waves. Often, a laser generates the plasma by directing the laser at a false target in proximity to the manufactured object. The plasma then hits the manufactured object, causing the thermal expansion and the ultrasonic wave.

The manufactured object may be composed of metal, composite, polymer, ceramic or any other materials. The detector may be one of several devices. For example, the detector may be a transducer on the surface of the object, a laser interferometer directed at the object, or a gas-coupled laser acoustic detector, to name a few.

The measured ultrasonic signals are analyzed to reconstruct physical attributes of the object that have a position or location with the object and a size. A combination of the optical penetration depth in the material given the generation-laser optical wavelength and of the temporal profile or pulse width of the generation-laser pulse dictate the frequency content of the laser-generated ultrasonic waves.

One problem associated with many typical ultrasound detectors is a poor signal-to-noise ratio (SNR) in the resulting signals. SNR is proportional to the amplitude of the sonic wave and inversely proportional to the square root of the bandwidth of the sonic wave. Many typical generation techniques produce low amplitude and/or broad bandwidth ultrasonic signals. These conditions lead to a reduced SNR and limit the quality of data acquired through such ultrasonic testing. In combination, these effects reduce the ability to detect features in the tested object. The reduced SNR in these typical sonic testing systems leads to corresponding reduced resolution in the resulting analysis. Smaller features like fractures may be difficult to detect with the reduced resolution. With the lower SNR of the typical systems, these smaller size features may go unnoticed.

When testing fails to detect features, these features may ultimately yield many problems, such as poor material performance or catastrophic failure of the part. When testing parts used in the airline industry, failure to detect flaws may lead to safety problems and costly accidents.

As such, many ultrasonic testing devices suffer from reduced SNR. Many other problems and disadvantages of the prior art will become apparent to one skilled in the art after comparing such prior art with the present invention as described herein.

SUMMARY OF THE INVENTION

Aspects of the invention are found in a system for generating an improved sonic response in a manufactured object. The system has a sonic energy signal generator, a model processor and a readable medium having a representation of the manufactured object. The model processor generates an optimized operating characteristic of the sonic energy signal generator from the representation of the manufactured object. The sonic energy signal generator is adjusted to reflect the optimized operating characteristics. Then, the sonic energy signal generator generates the particular sonic energy signal using the optimized operating characteristic.

Further, the system may have a programmable circuitry coupled to the model processor. The model processor may calculate the optimized operating characteristic with the programmable circuitry.

The system may also have a control circuitry. The control circuitry may adjust the sonic energy signal generator to reflect the optimized operating characteristic calculated by the model processor.

Further aspects of the invention are found in a system for adaptively testing or detecting a physical attribute in a manufactured object. The system has a sonic energy signal generator, a sonic energy signal measuring device, a signal analyzer and a model processor. The signal analyzer is coupled to the sonic energy signal measuring device. The model processor communicates with the signal analyzer. Furthermore, the model processor is coupled to the sonic energy signal generator.

In operation, the sonic energy signal generator generates a sonic energy signal in the manufactured object. The sonic energy signal measuring device measures the sonic energy signal. The signal analyzer analyzes the sonic energy signal to determine if the sonic energy signal is optimized.

If the sonic energy signal is not optimized, the model processor calculates optimized operating characteristics for the sonic energy signal generator. The sonic energy signal generator is then adjusted to reflect the optimized operating characteristics. Then, the sonic energy signal generator generates an improved sonic energy signal.

The system may have access to a representation of the manufactured object. The model processor may derive the optimized operating characteristic from the representation of the manufactured object.

The system may also have a programmable circuitry. The model processor may derive the optimized operating characteristics with the programmable circuitry. The programmable circuitry may be adaptable, and enable multiple instances of deriving the optimal operating characteristic of the sonic energy signal.

Additionally, the system may have a control circuitry. The control circuitry may adjust the sonic energy signal generator to reflect the optimized operating characteristics.

Another aspect of the invention may be found in a system for testing and/or detecting a physical attribute in an area of the manufactured object. Similar to the system above, the system includes a sonic energy signal generator, a sonic energy signal measuring device, a signal analyzer, and a model processor. A section in the area of the manufactured object is tested by generating a sonic energy signal. The sonic energy signal generator generates the sonic energy signal. The sonic energy signal is measured by the sonic energy signal measuring device.

Next, the signal analyzer determines if the signal is optimized. If the signal is not optimized, the model processor calculates an optimized operating characteristic of the sonic energy signal generator. Then, the sonic energy signal generator is adjusted to reflect the optimized operating characteristics and the section is retested. If the signal is optimized, the testing continues. If the signal is not optimized, the model processor calculates a new set of characteristics based on the signal just acquired.

As before, the system may have access to a representation of the manufactured object. The model processor may calculate the optimized operating characteristic from the representation of the manufactured object. The representation of the manufactured object may be a computer-aided-drafting representation of the manufactured object.

The system may also have a programmable circuitry. The model processor may calculate the optimized operating characteristic with the programmable circuitry.

Additionally, the system may have a control circuitry. The control circuitry may adjust the sonic energy signal generator to reflect the optimized operating characteristic.

The system may operate in other ways, as well. For example, the system may start with the retrieval of data such as the representation of the manufactured object. Then, the model processor may predetermine the optimized operating characteristics for the sonic energy signal generator from the data. Next, sonic energy signal generator may be adjusted to reflect the optimized operating characteristic.

Subsequently, the section may be tested. The signal analyzer may determine if the signal is optimized. If it is not optimized, the model processor may calculate new optimized operating characteristics. The sonic energy signal generator may be adjusted to reflect the new optimized operating characteristic.

If the signal is optimized, it may be determined whether the area of the manufactured object has been completely tested. If the area has been completely tested, the process ends. If not, a determination may be made as to whether a previously untested section requires different operating characteristics. If the previously untested section requires different operating characteristics, the model processor may calculate the operating characteristic.

Then, the sonic energy signal generator may be adjusted to reflect the operating characteristics. The previously untested section can then be tested.

If the section does not require another operating characteristic, the test of the previously untested section can be performed without adjusting the sonic energy signal generator. The process then proceeds as above.

Aspects of the invention may also be found in an exemplary embodiment. The system includes a laser generator, a laser interferometer, and a computer with a microprocessor and storage medium. The laser generator directs a laser pulse at an object. The pulse imparts energy to the object. The energy initiates a sonic energy signal. The laser interferometer measures the sonic energy signal. The computer acts as a signal analyzer to determine if the signal is optimized. Then, the computer acts as a model processor to determine optimized operating characteristics for the laser generator. The computer may determine the optimized operating characteristics from a ultrasonic wave generation and propagation model, a digital representation of the manufactured object, and the output of the signal analyzer. Next, the laser is adjusted to reflect the optimized operating characteristics. A subsequent sonic energy signal is initiated.

In the case of laser-ultrasound, several of the operating characteristics of the ultrasonic generator that may be optimized by the model processor include the temporal profile of the pulse, the optical wavelength, and the distribution of the laser beam at the part surface. Several of the part parameters that may influence the choice of the operating characteristics include the optical penetration depth, the thickness, the damage threshold, and the ultrasonic attenuation. The ultrasonic frequency range desired by the operator is another parameter that may influence the determination of the optimized characteristics by the model processor.

Several types and forms of mathematical models may be used by the invention. In one exemplary embodiment, the mathematical model may be an ultrasound generation model. In another exemplary embodiment, the mathematical model may be a propagation model. Many mathematical propagation models can be used, such as, for example:

M. Dubois, *Etude de la Generation des Ultrasons par Laser dans un Materiau Composite,* Ph.D dissertation, The University of Montreal (1994).

J. Spicer, *Laser Ultrasonics in Finite Structures: Comprehensive Modeling with Supporting Experiment,* Ph.D. dissertation, The John Hopkins University (1991) L. R. F. Rose, "Point-Source Representation for Laser Generated Ultrasound", *Journal of the Acoustical Society of America,* vol. 75, no. 3, pp. 723–732 (1984)

M. Dubois, P. W. Lorraine, A. S. Bauco, B. Venchiarutti, R. J. Filkins, T. E. Drake, and K. Yawn, "Optimization of temporal profile and optical penetration depth for laser-generation of ultrasound in polymer-matrix composites", in *Review of Progress in QNDE,* vol. 19, Edited by D. Thompson and D. E. Chimenti, Plenum Press, New-York, pp, 287–394 (2000)

A. D. W. McKie, J. W. Wagner, J. B. Spicer, and C. M. Penney, "Laser Generation of Narrow-Band and Directed Ultrasound", *Ultrasonics,* vol. 27, pp. 323–330 (1989) Y. H. Berthelot, "Themoacoustic Generation of Narrow-Band Signals with High Repetition Rate Pulsed Lasers", *Journal of the Acoustical Society of America,* vol. 85, no. 3, pp. 1173–1181 (1989).

As can be shown, several mathematical models can be used with the system, and others can be referenced from the literature. Of course, these may all be used in all forms and embodiments of the invention where a mathematical model is envisioned.

As such, a system for adaptively testing manufactured objects using ultrasound is described. Other aspects, advantages and novel features of the present invention will become apparent from the detailed description of the invention when considered in conjunction with the accompanying drawings.

DETAILED DESCRIPTION OF THE PREFERRED EMBODIMENT

Figure 1:
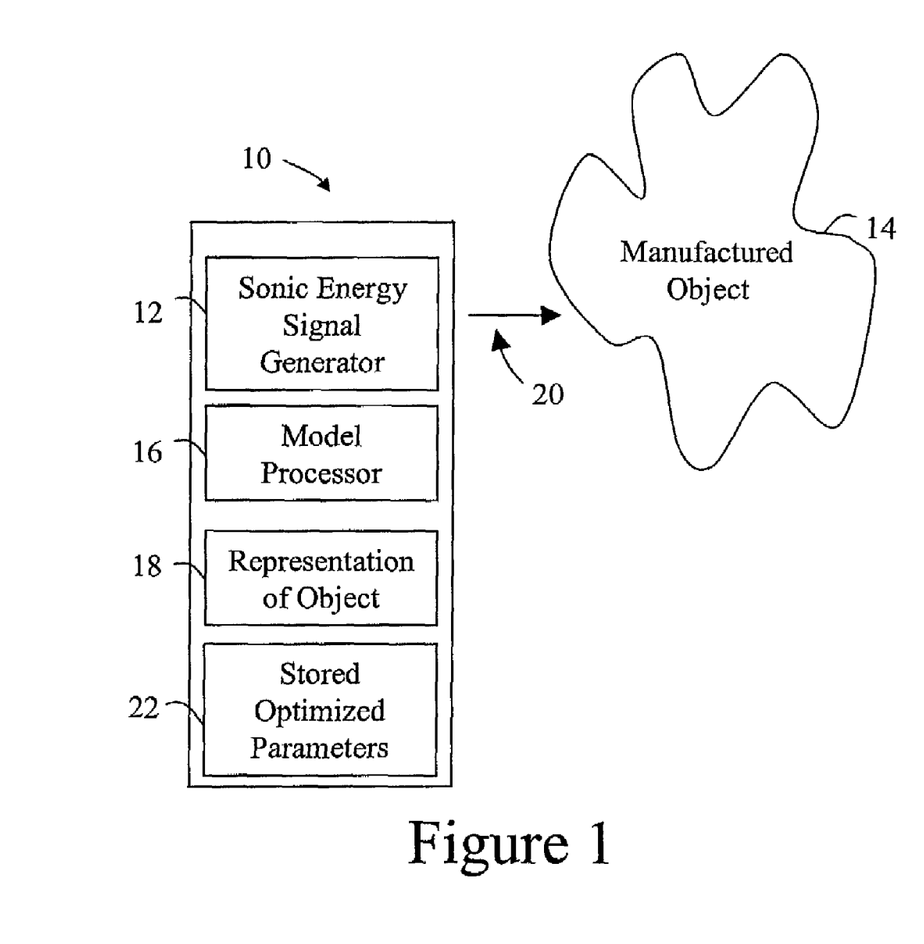
FIG. 1 is a schematic diagram of a system for generating an optimized sonic energy signal according to the invention.

FIG. 1 is a schematic diagram of a system for generating an optimized sonic energy signal according to the invention. The system 10 has a sonic energy signal generator 12, and a model processor 16. The model processor 16 has access to a representation of a manufactured object 18. In combination, these interact with the manufactured object 14, to produce the optimized sonic energy signal.

The system may interact in several configurations. For example, the model processor 16 may derive an optimized operating characteristic of the sonic energy signal generator 12 from the representation of the manufactured object 18. The sonic energy signal generator 12 may then interact with the manufactured object 14 to produce the optimized sonic energy signal. However, this example should not be considered limiting as the system may interact in other ways.

In another example, the model processor 16 may use properties of the sonic energy signal generator 12 in deriving the optimized operating state or characteristic. These properties may include limitations and boundaries of the operating states and characteristics, inputs to the sonic energy signal generator 12, outputs from the sonic energy signal generator 12, and others.

The sonic energy signal generator 12 may take one of several forms. For example, the sonic energy signal generator may be a transducer-induced ultrasonic wave generator, a laser ultrasound system, an electromagnetic acoustic transducer (EMAT), a plasma-induced ultrasound system, or others.

The model processor 16 may also take one of several forms. These forms may include a computer, an analog circuitry, a calculator, or a controller, among others.

The representation of the manufactured object 18 may be one of many types or a combination of types. These types may be a digital representation, a computer-aided-design (CAD) representation, a set of parameters, or others. The parameters may include physical properties, mechanical properties, thermal properties, thermo-acoustic properties, optical properties, and more. The representation may be derived or may be stored on a readable medium.

Each of the above components listed above may be housed together, separately or in any combination. They may be combined in the same equipment or exist as separate coupled units. For example, the model processor 16 may have network access to the representation of the manufactured object 18, or the representation of the manufactured object 18 may be stored locally, to name a few.

Figure 2:
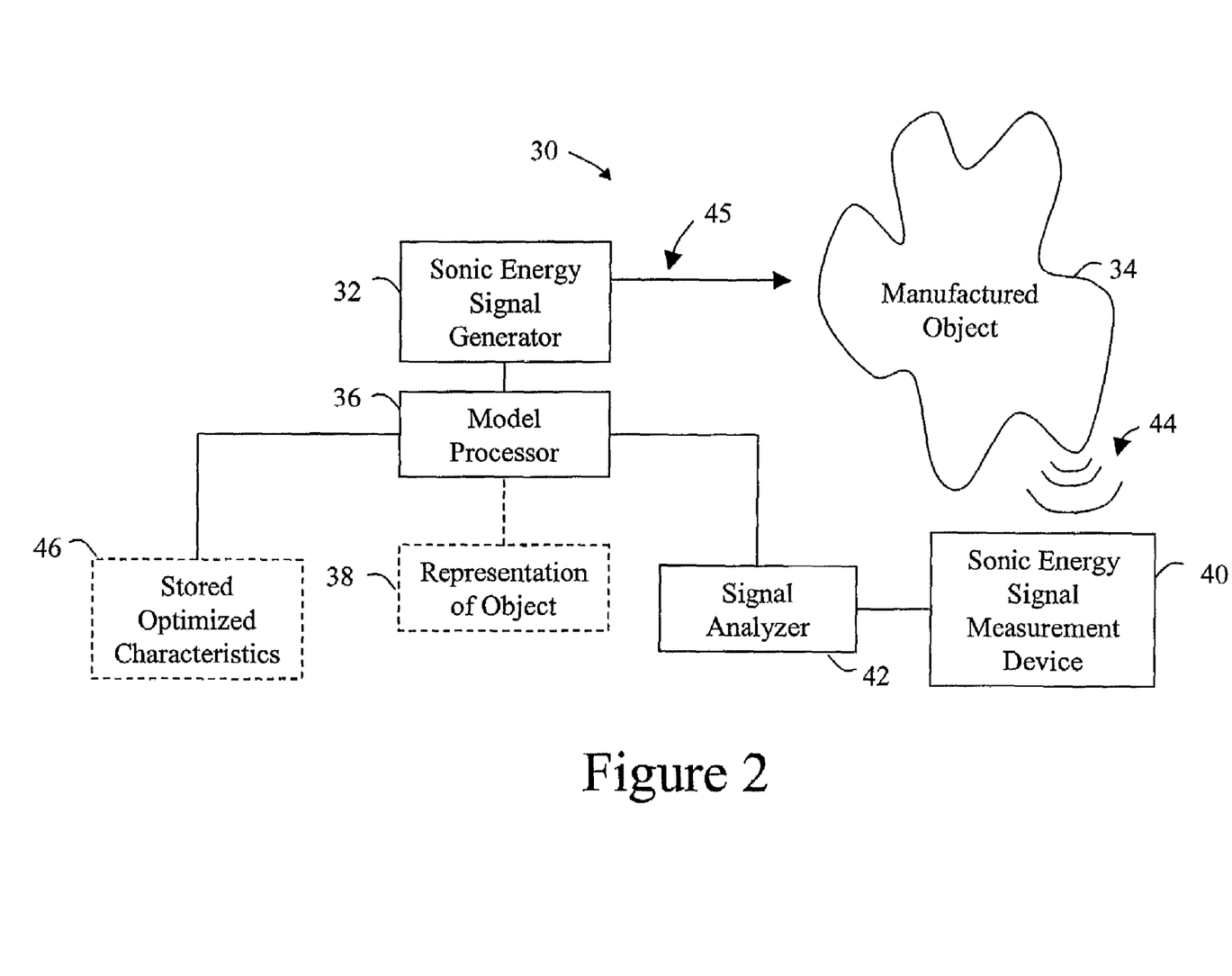
FIG. 2 is a schematic diagram of an exemplary embodiment of a system for adaptively generating a sonic energy signal according to FIG. 1.

FIG. 2 is a schematic diagram of an exemplary embodiment of a system for adaptively generating a sonic energy signal according to FIG. 1. Similar to the system of FIG. 1, the system 30 includes a sonic energy signal generator 32, a model processor 36. The system 30 also includes a signal analyzer 42 and a sonic energy signal measuring device 40. A representation of the manufactured object 38 may be included on an as needed basis. As before, each of the above components listed above may be housed together, separately or in any combination. They may be combined in the same equipment or exist as separate coupled units. For example, the model processor 36 may have network access to the representation of the manufactured object 38, or the representation of the manufactured object 18 may be stored locally, to name a few.

As before, the representation of the manufactured object 38 may be one of many types or a combination of types. These types may be a digital representation, a computer-aided-design (CAD) representation, a set of parameters, or others. The parameters may include physical properties, mechanical properties, thermal properties, thermoacoustic properties, optical properties, and more. The representation may be derived or may be stored on a readable medium.

The sonic energy signal measuring device 40 communicates with the signal analyzer 42. The signal analyzer 42 is in communication with the model processor 36. The model processor 36 is coupled to the sonic energy signal generator 32. The representation of the manufactured object 38 may be coupled to the model processor 36, where it is used to aid in deriving the optimal characteristic, as described above.

In operation, the sonic energy signal generator 32 interacts with the manufactured object 34 to produce a sonic energy signal 44. The interaction is depicted as a line 45. The sonic energy signal measuring device 40 detects and measures the sonic energy signal 44 about the manufactured object. The term "about" can mean in, on, or in proximity to, among others. The sonic energy signal measuring device 40 produces a measured signal. Then, the signal analyzer 42 analyzes the measured signal and produces an output. The model processor 36 determines an optimized operating characteristic from the output of the signal analyzer 42. Then the sonic energy signal generator 32 interacts with the manufactured object 34 using the optimized operating characteristic.

In one exemplary embodiment, the sonic energy signal generator 32 is a laser pulse generator with several operating characteristics. The laser pulse generator may take many forms. These forms may include a ruby laser, $CO_2$ laser, Nd:YAG laser, Yb:YAG laser, Nd:YVO$_4$ laser, Nd:YLF laser, Tm:YLF laser, Ho:YLF laser, Ho:YAG laser, alexandrite laser, excimer laser, and titanium sapphire laser.

The operating characteristics may take many forms. The operating characteristics may be optical wavelength, pulse temporal profile, power, beam shape, beam size, time delay between pulses, and others.

The laser pulse generator directs a first laser pulse at the manufactured object 34. The pulse imparts energy to the manufactured object 34. This energy initiates a sonic energy signal 44. Then the sonic energy signal 44 is measured by a sonic energy signal measuring device 40.

The sonic energy signal measuring device 40 may, for example, be a laser interferometer, like a confocal Fabry-Perot interferometer, a Michelson interferometer, or a photorefractive two-wave mixing interferometer, to name a few. The sonic energy signal measuring device 40 produces a measured signal. Then, the signal analyzer 42 analyzes the measured signal and produces and output. The model processor 36 determines an optimized operating characteristic from the output of the signal analyzer 42 and using the representation of the manufactured object 38. Then the laser pulse generator generates a second laser pulse using the optimized operating-characteristics. The second pulse is directed at the manufactured object 34 and imparts a new energy to the manufactured object 38. This new energy initiates an improved sonic energy signal.

The model processor 36 may, for example derive an optimal wavelength by solving an optimization routine having a propagation model and a generation model. The model processor 36 may modify the optical wavelength of the generating laser by tuning a device like an optical parametric oscillator. Further, the optical wavelength may be altered by one or more devices about the laser generator. These devices may include an optical parametric oscillator, an optical parametric amplifier, a Raman cell, a Brillouin cell, a difference frequency mixing setup, a sum frequency mixing setup, a harmonic generation setup, and a combination of an optical parametric oscillator and a difference frequency mixing setup, among others. In addition, the optical wavelength can also be modified using methods described in U.S. Pat. No. 6,176,135.

As a result, the laser may produce a pulse with an optimal wavelength. Further, the laser pulses separation may be altered using the methods described in U.S. Pat. No. 6,668,654.

The process may start with the model processor 36 determining a first guess at an optimized operating characteristic using the representation of the manufactured object 38. Then, the laser generator produces the first laser pulse with the first guess at the optimized operating characteristic.

The process may involve several iterative steps until achieving a predefined criteria before generating the improved sonic energy signal. The more than one sonic energy signal may be used in determining the optimized operating characteristic.

The system may be automated, thus allowing the components to interact automatically. Or, the system may contain human intervention steps.

Further, the derived optimal characteristic and/or the optimized operating characteristic may be stored. The stored optimal characteristics and/or the optimized operating characteristics may be used at a later time to aid in testing similar objects. For example, a measurement of an improved sonic energy signal may be used later for comparing measurements of like objects. In another example, optimal operating characteristics of a laser may be used for later tests of like objects without going through the iterative steps of optimization.

The sonic energy signal generator 32 may take may other forms as well. These forms may include a transducer, a plasma device, a carbon dioxide laser, a Nd:YAG laser, a ruby laser, a Yb:YAG laser, a Nd:YVO$_4$ laser, a Nd:YLF laser, a Tm:YLF laser, a Ho:YLF laser, a Ho:YAG laser, an alexandrite laser, an excimer laser, a titanium sapphire laser and others. The sonic energy generator 32 may also be any other device that can produce electromagnetic pulsed energy like, but not limited to, an optical parametric oscillator.

The sonic energy signal measuring device 40 may also take many forms. These forms may include one or more transducers, a gas-coupled laser acoustic detector, and a laser interferometer, among others. Further, the sonic energy signal measuring device may be an interferometer selected from a group consisting of a confocal Fabry-Perot interferometer, a photorefractive two-wave mixing interferometer, a Michelson interferometer, a Mach-Zender interferometer, and a Sagnac interferometer, among others.

The signal analyzer 42 may be one of several devices or a combination of devices. These devices may include a computer with a microprocessor, an analog circuit, a controller, an oscilloscope, and others. The output from the signal analyzer may be a signal indicative of a detected physical attribute, a signal indicative of the SNR of the sonic energy signal, a binary signal, a lack of a signal, or others.

The model processor 36 may also be one of several devices or a combination of devices. These may include a computer with a microprocessor, an analog circuitry, a controller, and others. The model processor and the signal analyzer 42 may be encompassed by the same equipment, separate equipment or combined with other devices.

The representation of the manufactured object 38 may take several forms or a combination of forms. These forms may include a digital form, a CAD representation and a set of parameters, among others. This set of parameters may include one or more of material properties, mechanical properties, thermal properties, optical properties, acoustic properties, and others. The representation of the manufactured object 38 may be in communication with the model processor 36 and/or the signal analyzer 42. Either or both of the model processor 36 and the signal analyzer 42 may use the representation of the manufactured object 38 to perform their respective functions.

Figure 3:
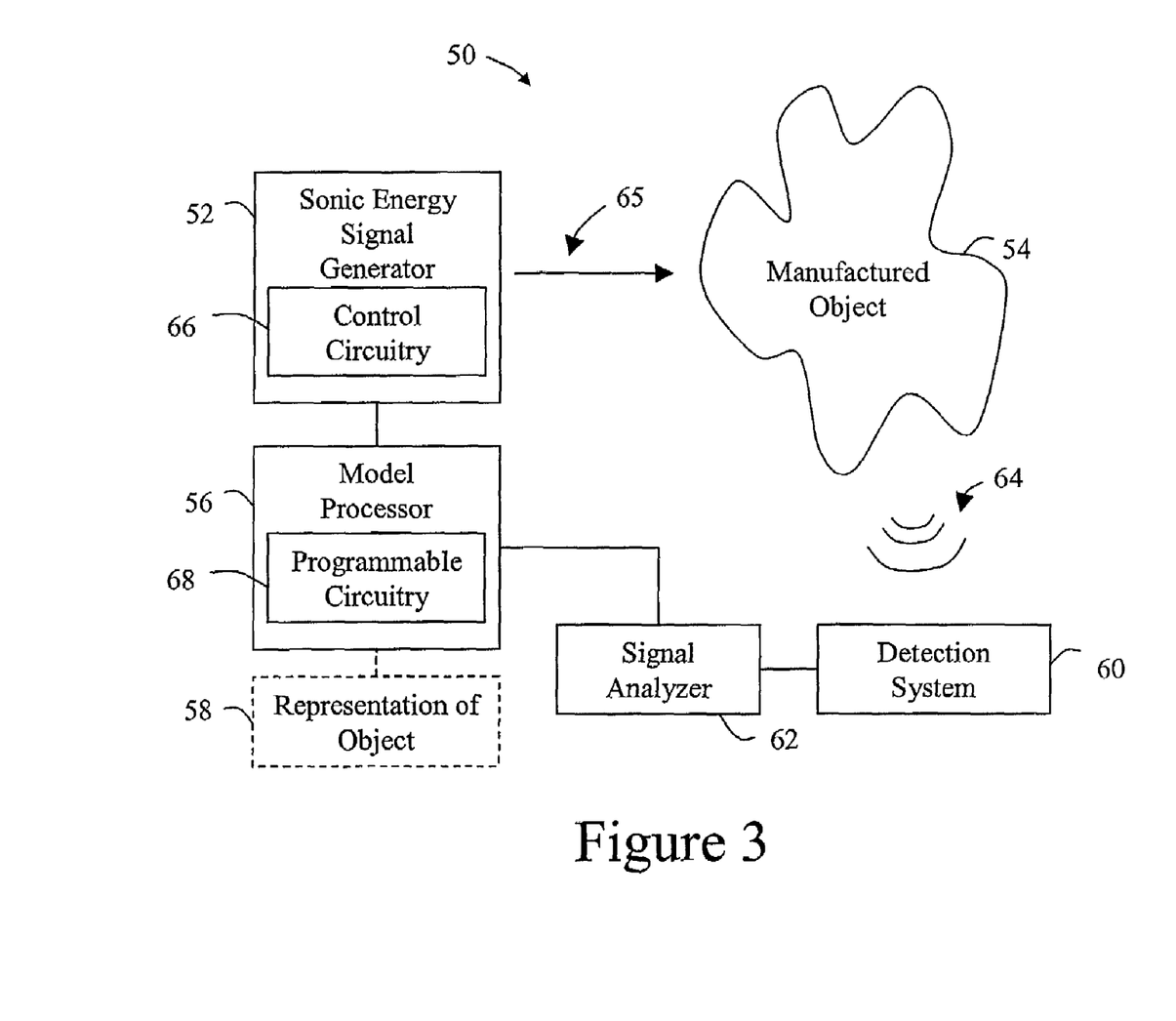
FIG. 3 is a schematic diagram of another exemplary embodiment of a system for adaptively generating a sonic energy signal according to FIG. 1.

FIG. 3 is a schematic diagram of another exemplary embodiment of a system for adaptively generating a sonic energy signal according to FIG. 1. Similar to the system of FIG. 2, the system 50 of FIG. 3 includes a sonic energy signal generator 52, a model processor 56, a signal analyzer 62 and a sonic energy signal measuring device. In this figure, the sonic energy signal measuring device is represented by a detection system 60. As in the system of FIG. 2, the system

50 may also include a representation of the manufactured object 58. In addition, this embodiment depicts a control circuitry 66 and a programmable circuitry 68.

The detection system 60 communicates with the signal analyzer 62. The signal analyzer 62 is in communication with the model processor 56. The model processor may be coupled to the sonic energy signal generator. The programmable circuitry 68 may be attached to the model processor 56. The control circuitry 66 may be attached to the sonic energy signal generator 52.

Despite the depiction, the programmable circuitry 68 may be separate or included in the model processor 56. Similarly, the control circuitry 66 may be separate or attached to the sonic energy signal generator 52. The control circuitry 66 may also be attached to the model processor 56.

The representation of the manufactured object 58 is depicted as being in communication with the model processor 56. However, in other configurations, it may communicate with the signal analyzer 62 or both the model processor 56 and the signal analyzer 62.

This system 50 operates similar to the system of FIG. 2. The sonic energy signal generator 52 has an operating characteristic. With the initial operating characteristic, the sonic energy signal generator 52 interacts with manufactured object 54 to initiate a sonic energy signal 64 in the manufactured object. The detection system 60 detects and measures the sonic energy signal 64 and produces a measured signal. The signal analyzer 62 analyzes the measured signal and produces an output. The model processor 56 determines an optimized operating characteristic using the output from the signal analyzer 62. Then, the sonic energy signal generator interacts with manufactured object 54 to produce an improved sonic energy signal.

The process may also start with model processor 56 generating the initial operating characteristic. The model processor 56 may determine the optimized operating characteristic from the representation of the manufactured object 58. The model processor may also determine the optimized operating characteristic with the programmable circuitry 68. In addition, the control circuitry 66, may be used to adjust the initial operating characteristic to the optimized operating characteristic.

The sonic energy signal generator 52 may take may other forms as well. These forms may include a transducer, a plasma device, a carbon dioxide laser, a Nd:YAG laser, a ruby laser, a Yb:YAG laser, a Nd:YVO$_4$ laser, a Nd:YLF laser, a Tm:YLF laser, a Ho:YLF laser, a Ho:YAG laser, an alexandrite laser, an excimer laser, a titanium sapphire laser, and others. The sonic energy generator 52 may also be any other device that can produce electromagnetic pulsed energy like, but not limited to, an optical parametric oscillator.

The detection system 60 may also take many forms. These forms may include one or more transducers, a gas-coupled laser acoustic detector, and a laser interferometer, among others. The interferometer may take many forms. These forms may include a confocal Fabry-Perot interferometer, a photorefractive two-wave mixing interferometer, a Michelson interferometer, a Mach-Zender interferometer, and a Sagnac interferometer, among others.

The signal analyzer 62 may be one of several devices or a combination of devices. These devices may include a computer with a microprocessor, an analog circuit, a controller, an oscilloscope, and others.

The model processor 56 may also be one of several devices or a combination of devices. These may include a computer with a microprocessor, an analog circuitry, a controller, and others. The model processor 56 and the signal analyzer 62 may be encompassed by the same equipment, held separately, or combined with other devices. The model processor may use a model to determine an expected result.

Several types and forms of mathematical models may be used by the invention. In one exemplary embodiment, the mathematical model may be an ultrasound generation model. In another exemplary embodiment, the mathematical model may be a propagation model. Many mathematical propagation models can be used, such as, for example:

M. Dubois, *Etude de la Generation des Ultrasons par Laser dans un Materiau Composite,* Ph.D dissertation, The University of Montreal (1994).

J. Spicer, *Laser Ultrasonics in Finite Structures: Comprehensive Modeling with Supporting Experiment,* Ph.D. dissertation, The John Hopkins University (1991) L. R. F. Rose, "Point-Source Representation for Laser Generated Ultrasound", *Journal of the Acoustical Society of America,* vol. 75, no. 3, pp. 723–732 (1984)

M. Dubois, P. W. Lorraine, A. S. Bauco, B. Venchiarutti, R. J. Filkins, T. E. Drake, and K. Yawn, "Optimization of temporal profile and optical penetration depth for laser-generation of ultrasound in polymer-matrix composites", in *Review of Progress in QNDE,* vol. 19, Edited by D. Thompson and D. E. Chimenti, Plenum Press, New-York, pp, 287–394 (2000)

A. D. W. McKie, J. W. Wagner, J. B. Spicer, and C. M. Penney, "Laser Generation of Narrow-Band and Directed Ultrasound", *Ultrasonics,* vol. 27, pp. 323–330 (1989) Y. H. Berthelot, "Themoacoustic Generation of Narrow-Band Signals with High Repetition Rate Pulsed Lasers", *Journal of the Acoustical Society of America,* vol. 85, no. 3, pp. 1173–1181 (1989).

As can be shown, several mathematical models can be used with the system, and others can be referenced from the literature. Of course, these may all be used in all forms and embodiments of the invention where a mathematical model is envisioned.

The model processor 56 may determine the optimized operating characteristic through several means. These means may include solving a wave propagation model, determining peak locations and amplitudes, optimizing a operating characteristic to enhance an expected sonic signal given a wave generation model, and more.

The representation of the manufactured object 58 may take several forms or a combination of forms. These forms may include a digital form, a CAD representation and a set of parameters, among others. This set of parameters may include one or more of material properties, mechanical properties, thermal properties, optical properties, acoustic properties, and others.

The programmable circuitry 68 may be reprogrammed with a hand held device, over a network, by direct action through a keyboard, or through other means. The outcome is an adaptable circuitry and an adaptable system 50. Other programmable circuitry depicted in other figures may be dynamically changed in a similar manner.

The control circuitry 66 acts to adjust the operating characteristics of the sonic energy signal generator 52. The control circuitry may perform in several ways. For example, it may take a signal from the model processor 56 and adjust the sonic energy signal generator 52 according to the signal. The signal from the model processor 56 may be a voltage setting, a specified operating parameter, or a current signal, to name a few. The control circuitry 66 may then use the signal to adjust a parameter on the sonic energy signal generator 52. This parameter may be a voltage to a pumping medium, a mirror position, an aperture opening, a signal to an acoustooptic cell, those methods of U.S. Pat. No. 6,176,135 or others. In this manner, the control circuitry may adjust the operating characteristics of the sonic energy signal generator 52. The operating characteristics may be optical wavelength, beam shape, beam size, pulse temporal profile, power, or time delay between successive pulses.

The control circuitry may be implemented in several ways. These ways may include a computer, a handheld circuitry that executes software instructions, or an implementation in hardware.

Figure 4:
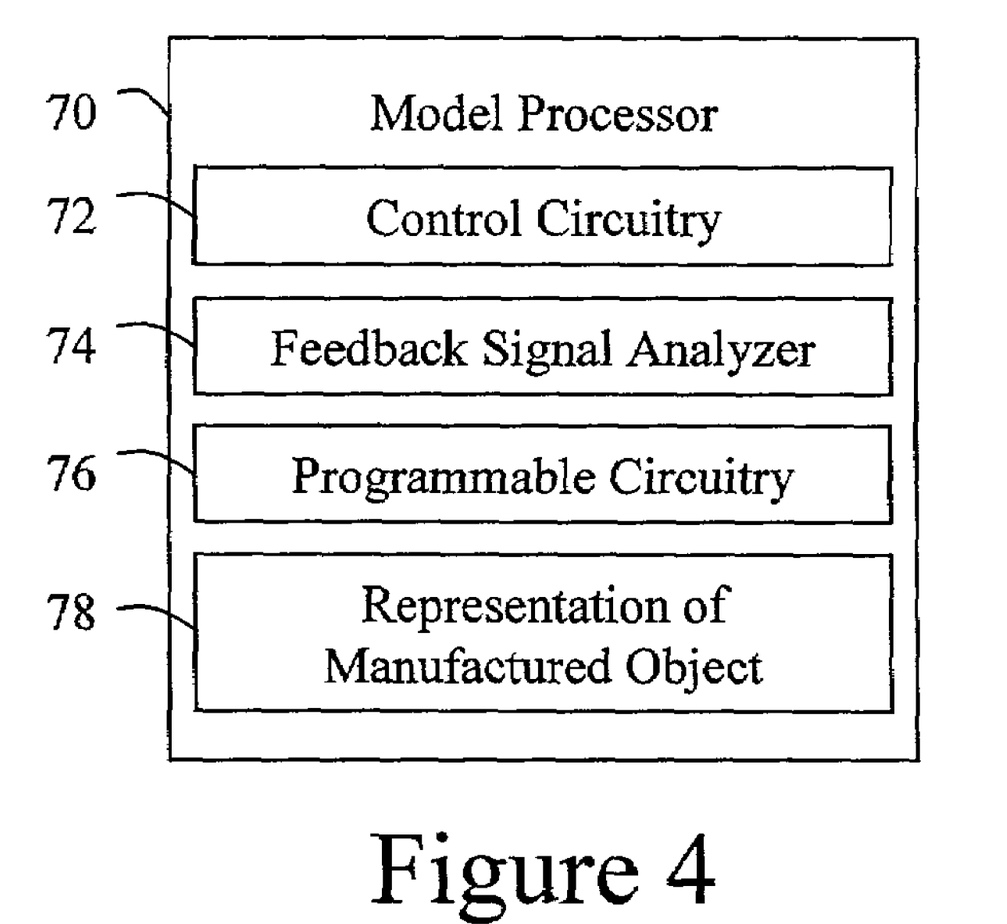
FIG. 4 is a schematic block diagram depicting an exemplary apparatus that may be used by the system of FIG. 1.

FIG. 4 is a schematic block diagram depicting an exemplary apparatus that may be used by the system of FIG. 1. The model processor 70 has a control circuitry 72, a signal analyzer 74, a programmable circuitry 76, and a representation of the manufactured object 78. Each of the control circuitry 72, signal analyzer 74, programmable circuitry 76, and representation of the manufactured object 78 may perform the functions described in the discussions above, respectively.

In this embodiment, each is depict as being incorporated in the model processor 70. However, all, some or none may be incorporated in the model processor 70. Each may be included on an as needed basis.

In an exemplary embodiment, the model processor 70 may be a computer with a microprocessor. The control circuitry may act as an interface between the model processor 70 and a sonic energy signal generator. The signal analyzer 74 may interface the model processor 70 with a sonic energy signal measuring device. Through this interface, the signal analyzer 74 may, for example, analyze a measured signal from the sonic energy signal measuring device. From this analysis, the signal analyzer may determine a set of specific values.

The programmable circuitry 76 may incorporate software. This software may, for example, optimize an expected sonic energy signal by varying an operating characteristic of a sonic energy signal generator. The software may perform the optimization using a given model, the set of specific values from the signal analyzer 74 and the representation of the manufactured object 78. Then the software may produce a result. Next, this result may be used by the control circuitry to adjust the sonic energy signal generator.

In a specific embodiment, software run on a computer with a microprocessor may determine an optimized wavelength for a laser ultrasound testing device by solving an ultrasound generation and propagation model. This model may require specific inputs such as previous amplitudes, acoustic properties of the manufactured object, optical properties of the manufactured object, and information about the laser ultrasound testing device, among others. The software may use information from the signal analyzer 74 to acquire ultrasonic signal amplitude. The software may also use a CAD representation of the manufactured object in conjunction with acoustic and optical property data to determine the optimized wavelength. Then, the software may direct the control circuitry to adjust the laser ultrasound testing device, accordingly. This example is only one possible embodiment of an apparatus for use in the invention. Many other configurations may be used and the invention is not limited to this embodiment. This model processor may be one such processor, or it may exist across multiple computing devices.

Figure 5:
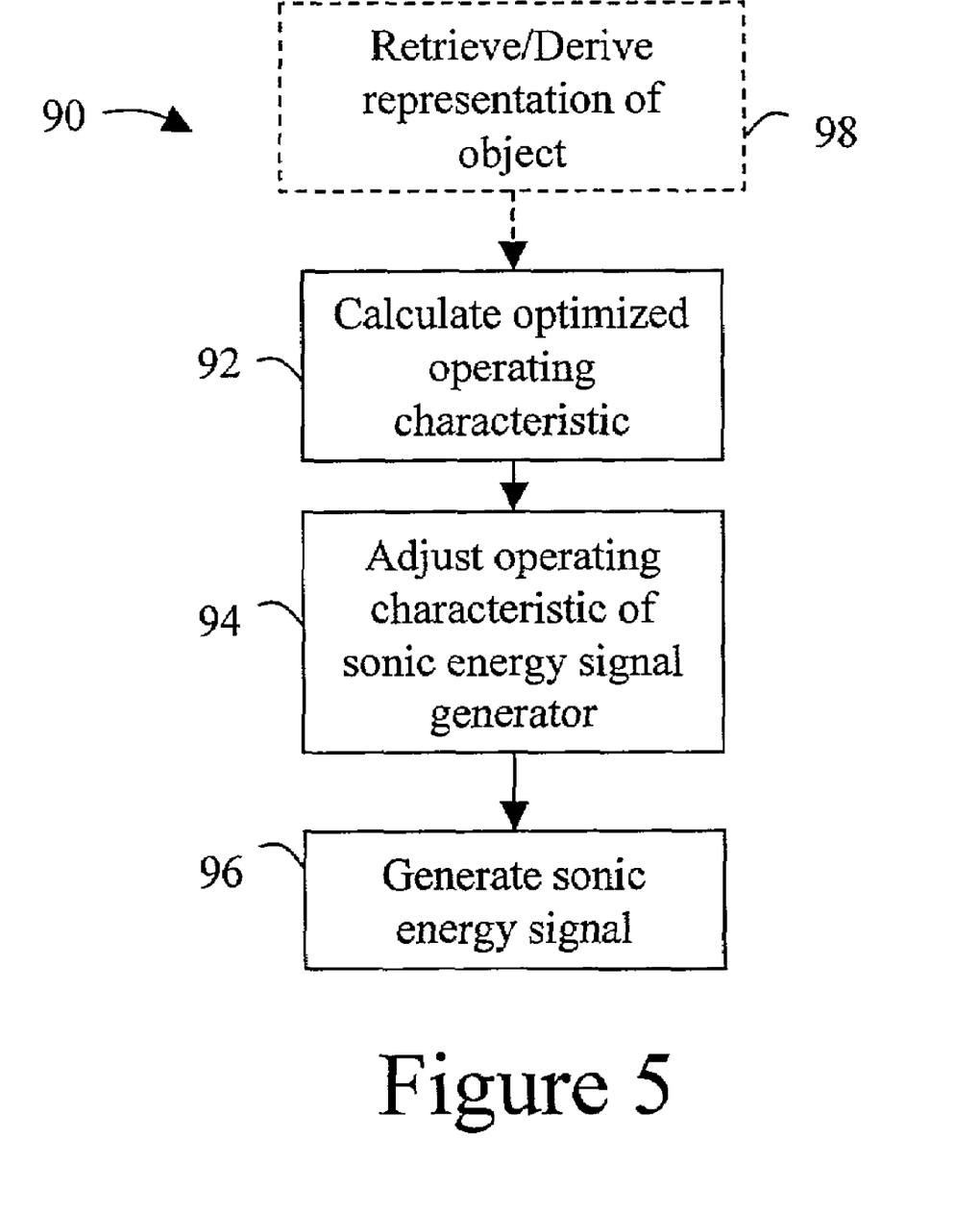
FIG. 5 is a block flow diagram depicting an exemplary method that may be used by the system of FIG. 1.

FIG. 5 is a block flow diagram depicting an exemplary method that may be used by the system of FIG. 1. In a block 92, an optimized operating characteristic of a sonic energy signal generator is calculated. Then, as seen in a block 94, the operating characteristic of the sonic energy signal generator is adjusted. Finally, in a block 96, the sonic energy signal generator with the optimized operating-characteristic generates an optimized sonic energy signal.

The method may also incorporate a step represented by a block 98. A representation of the manufactured object is retrieved. The optimized operating characteristic may be generated from the representation of the manufactured object.

Figure 6:
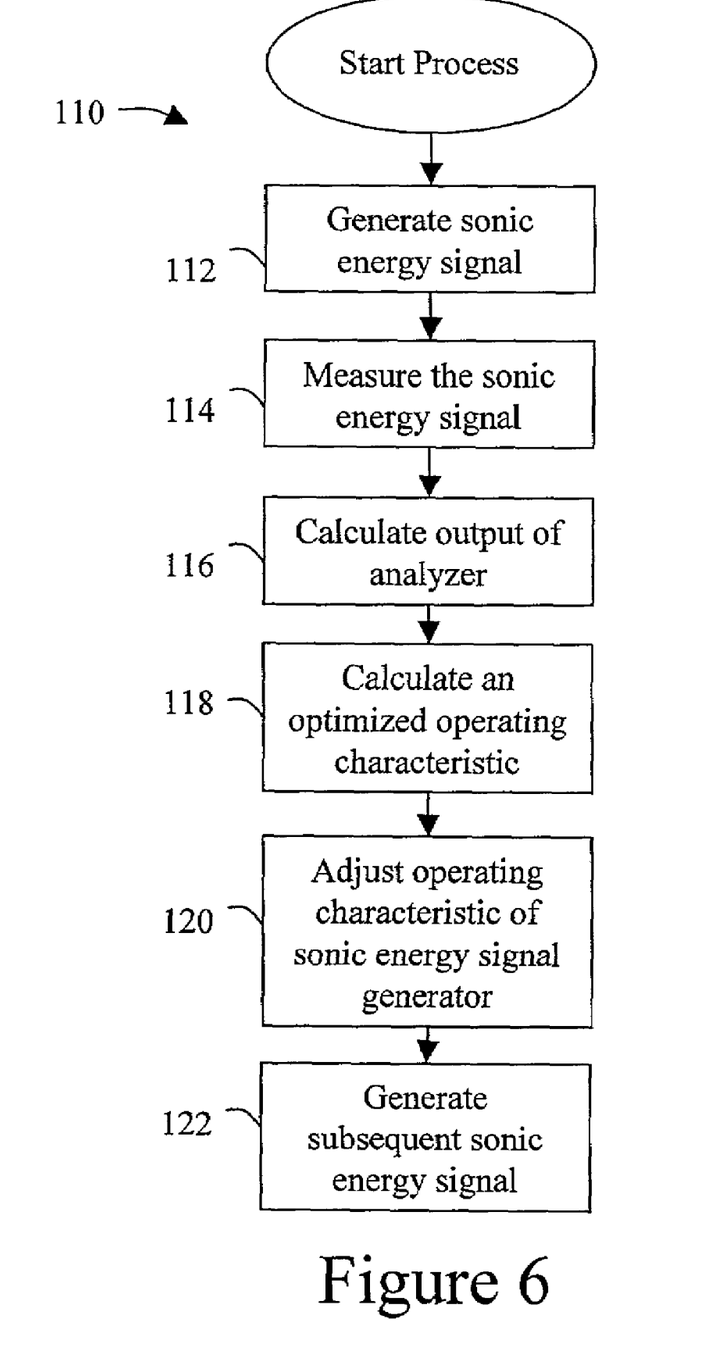
FIG. 6 is a block flow diagram depicting an exemplary method that may be used by the systems of FIG. 2 and FIG. 3.

FIG. 6 is a block flow diagram depicting an exemplary method that may be used by the systems of FIG. 2 and FIG. 3. In a block 112, a sonic energy signal is generated. In another block, the sonic energy signal is measured. In a further block 116, an output of a signal analyzer is calculated. The output may be calculated from the measured sonic energy signal.

Next, in a block 118, an optimized operating characteristic of a sonic energy signal generator is calculated. The optimized operating characteristic may be calculated from the output of the signal analyzer.

Subsequently, in a block 120, the sonic energy signal generator is adjusted to reflect the calculated optimized operating characteristic. In another block 122, a subsequent sonic energy signal is generated using the sonic energy signal generator adjusted to reflect the optimized operating characteristic. The subsequent sonic energy signal need not be consecutive to the measured sonic energy signal. The sonic energy signal generator may generate a plurality of sonic energy signals. These sonic energy signals may also be used in determining the optimized operating characteristic of the sonic energy signal generator.

Further, the derived optimal characteristic and/or the optimized operating characteristic may be stored. The stored optimal characteristic and/or the optimized operating characteristic may be used at a later time to aid in testing similar objects. For example, a measurement of an improved sonic energy signal may be used later for comparing measurements of like objects. In another example, a optimal operating characteristic of a laser may be used for later tests of like objects.

Figure 7:
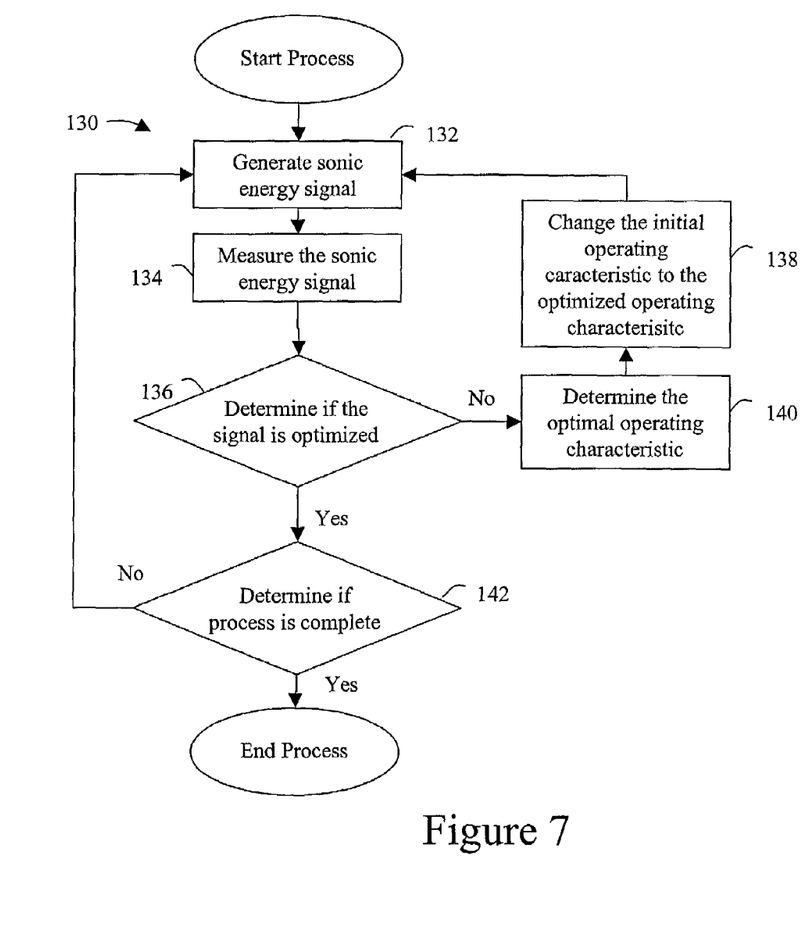
FIG. 7 is a block flow diagram depicting another exemplary method that may be used by the systems of FIG. 2 and FIG. 3.

FIG. 7 is a block flow diagram depicting another exemplary method that may be used by the systems of FIG. 2 and FIG. 3. The method 130 tests a physical attribute in an area on a manufactured object. In a block 132, a sonic energy signal is generated within a section in the area of the manufactured object using a sonic energy signal generator. In another block 134, the sonic energy signal is measured with a sonic energy signal measuring device.

Next, in a block 136, a signal analyzer determines if the signal is optimized. An optimized signal may be a signal that meets an SNR requirement, meets a certain resolution threshold, or accurately detects a physical attribute, among others. If the signal is not optimized, in a block 140, optimized operating characteristic of the sonic energy signal generator are determined. Then, in a block 138, the sonic energy signal generator is adjusted to reflect the determined optimized operating characteristic. A subsequent sonic energy signal is then generated.

If the signal is optimized, in a block 142, it is determined if the area has been completely tested. If the area has been completely tested, the process ends. If not, a new section within the area is tested by generating a subsequent sonic energy signal.

In this manner, the sonic energy signal can be adapted to improve SNR. It may also be adapted to test smaller features where needed. Through adaptively improving the sonic energy signal, more accurate tests can be performed. These more accurate tests may lead to better detection of defects and flaws. In an industry like aircraft servicing, better defect detection will improve safety and prevent catastrophic failures.

Figure 8:
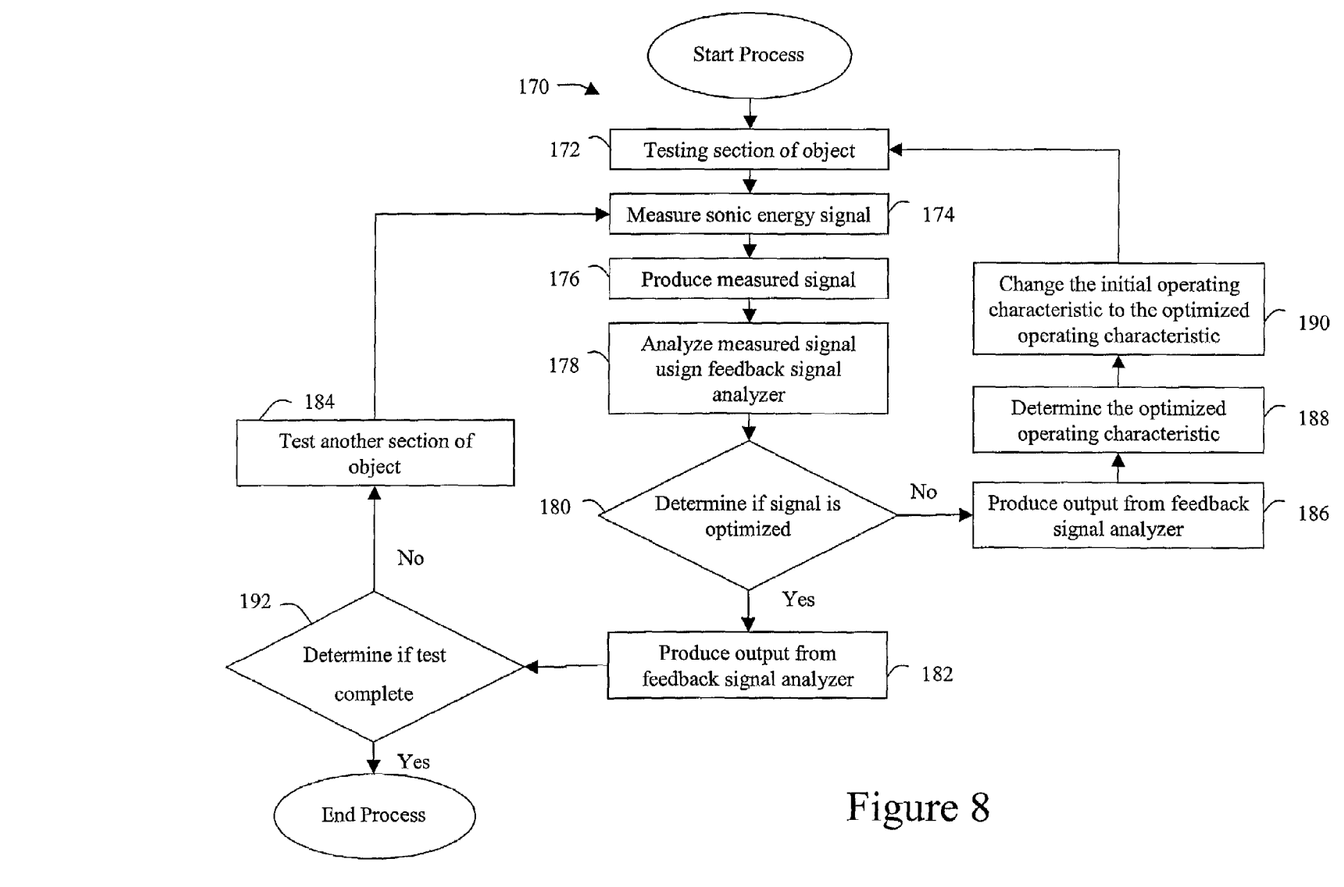
FIG. 8 is another block flow diagram of an exemplary method that may be used by the systems of FIG. 2 and FIG. 3.

FIG. 8 is another block flow diagram of an exemplary method that may be used by the systems of FIG. 2 and FIG. 3. Similarly to the method of FIG. 7, a method 170 tests a physical attribute in an area of a manufactured object. In a block 172, a section of the manufactured object is tested by generating a sonic energy signal within the section using a sonic energy signal generator. In another block 174, the sonic energy signal is measured by a sonic energy signal measuring device. Next, in a block 176, the sonic energy signal measuring device produces a measured signal.

Then, in a block 178, a signal analyzer analyzes the measured signal. In a block 180, the analysis of the measured signal is used to determine if the signal is optimized. An optimized signal may be a signal that meets an SNR requirement, meets a certain resolution threshold, or accurately detects a physical attribute, among others. If the signal is not optimized, in a block 186, the signal analyzer produces an output. In a block 188, a model processor determines an optimized operating characteristic of the sonic energy signal generator using the output from the signal analyzer. Then, in a block 190, the sonic energy signal generator is adjusted to reflect the determined optimized operating characteristic. The model processor or a control circuitry may be used to adjust the sonic energy signal generator.

If the signal is optimized, in a block 182, the signal analyzer produces an output indicating the signal is optimized. Next, in a block 192, it is determined if the area of the manufactured object has been completely tested. If the area has been completely tested, the process ends. If not, in a block 184, a previously untested section of the object is tested. A model processor or a control circuitry may be used to determine if the area has been completely tested.

Using the method described above, physical attributes in an area of a manufactured object may be tested. Certain physical features, such as flaws and defects, may also be detected. As described previously, by automatically and adaptively testing manufactured objects more accurate detection of defects will be accomplished. This more accurate detection will lead to improved safety and prevent catastrophic failures in many industries.

Figure 9:
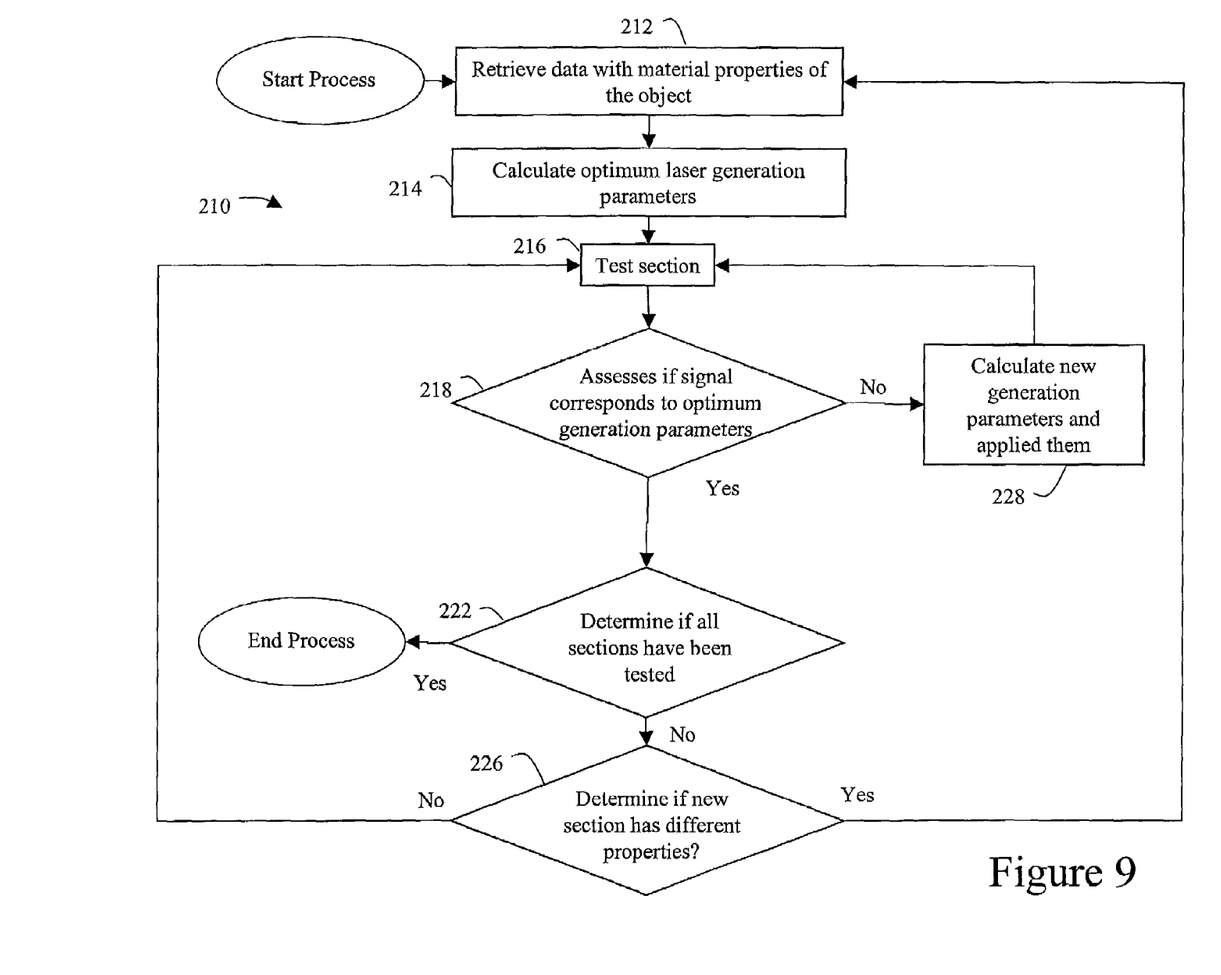
FIG. 9 is a further block flow diagram of another exemplary method that may be used by the systems of FIG. 2 and FIG. 3.

FIG. 9 is a further block flow diagram of another exemplary method that may be used by the systems of FIG. 2 and FIG. 3. Similar to the method of FIG. 8, this method 210 tests an area of a manufactured object. However, this method includes extra steps that predetermine an optimized operating characteristic when a previously untested section is to be tested.

In a block 212, data associated with and the material properties of the manufactured object in a section within an area of the manufactured object are retrieved. In another block 214, a model processor calculates the optimized operating characteristic of a sonic energy signal generator. The model processor may generate the optimized operating characteristic from the retrieved data.

Next, in a block 216, the section is tested by generating a sonic energy signal with the sonic energy signal generator having the optimized operating characteristic. The sonic energy signal is measured with a sonic energy signal measuring device.

In a block 218, the signal is assessed to determine if the signal corresponds to an optimal operating characteristic. A signal analyzer may perform this assessment. If the signal does not correspond to an optimal operating characteristic, in a block 228, new optimized operating characteristic of the sonic energy signal generator are calculated and applied to the sonic energy signal generator. The new optimized operating characteristic may be calculated with a model processor. The model processor or a control circuitry may apply the new optimized operating characteristic to the sonic energy signal generator. Then, the section is retested.

If the signal does correspond to an optimal operating characteristic, in a block 222, a determination is made as to whether the area has been completely tested. This determination may be made by the signal analyzer, the model processor or the control circuitry. If the area has been completely tested, the process is ended.

If the area has not been completely tested, in a block 226, it is determined if the new section to be tested requires a new operating characteristic. This determination may be made by a model processor, a signal analyzer, or a control circuitry. For example, the model processor may determine if the new section requires a new operating characteristic by comparing the data about the tested section to data about the new section. If the new section does not require a new operating characteristic, the section is tested. However, if the section does require a new operating characteristic, data associated with the new section is retrieved. Then, a new optimized operating characteristic is calculated and the new section is tested.

In this manner, the sonic energy signal can be adapted to improve SNR. It may also be adapted to test smaller features where needed. Through adaptively improving the sonic energy signal, more accurate tests can be performed. These more accurate tests lead to better detection of defects and flaws. In an industry like aircraft servicing, better defect detection will improve safety and prevent catastrophic failures. In material research, this method may lead to improvements in advanced materials.

As such, a system and method for adaptively testing a physical attribute of a manufactured object using a sonic energy signal is described. In view of the above detailed description of the present invention and associated drawings, other modifications and variations will now become apparent to those skilled in the art. It should also be apparent that such other modifications and variations may be effected without departing from the spirit and scope of the present invention as set forth in the claims which follow.

What is claimed is:

1. A ultrasonic testing system operable to generate and sample sonic energy signal(s) in a manufactured object that results in an improved signal to noise ratio (SNR) within the sampled sonic energy signal(s), comprising:

a sonic energy signal generator having a set of operating characteristic(s), wherein the sonic energy signal generator is operable to generate sonic energy signals within the manufactured object, and wherein the ultrasonic testing system is operable to sample these sonic energy signals; and a model processor, communicatively coupled to the sonic energy signal generator, wherein the model processor operable to determine a set of operating characteristic(s) that result in the improved SNR of the sampled sonic energy signals, and wherein the sonic energy signal generator is operable to generate the sonic energy signal(s) within the manufactured object based on the determined set of operating characteristic(s) that result in the improved SNR of the sampled sonic energy signals.

2. The ultrasonic testing system of claim 1, the system further comprising:
a representation of the manufactured object accessible to the model processor; and
the model processor operable to determine a set of operating characteristic(s) that result in the improved SNR of the sampled sonic energy signals from the representation of the manufactured object.

3. The ultrasonic testing system of claim 2 wherein the representation of the manufactured object is a CAD model.

4. The ultrasonic testing system of claim 1, the system further comprising:
a sonic energy signal measuring device;
a signal analyzer communicatively coupled to the sonic energy signal measuring device;
the model processor communicatively coupled to the signal analyzer;
the sonic energy signal measuring device measuring the sonic energy signal(s);
the signal analyzer analyzing the measured sonic energy signal(s); and
the model processor deriving the operating characteristic for the sonic energy signal generator based on an output of the signal analyzer.

5. The ultrasonic testing system of claim 4 wherein the sonic energy signal measuring device comprises an interferometer selected a group consisting of a confocal Fabry-Perot interferometer, a photorefractive two-wave mixing interferometer, a Michelson interferometer, a Mach-Zender interferometer, and a Sagnac interferometer.

6. The ultrasonic testing system of claim 1, the system further comprising:
a programmable circuitry communicatively coupled to the model processor; and
the model processor deriving the operating characteristic using the programmable circuitry.

7. The ultrasonic testing system of claim 1 wherein the set of operating characteristic(s) of the sonic energy signal generator are changed to match the determined set of operating characteristic(s) that result in the improved SNR of the sampled sonic energy signals.

8. The ultrasonic testing system of claim 1, the system further comprising:
a control circuitry communicatively coupled to the sonic energy signal generator;
the control circuitry communicatively coupled to the model processor; and
the control circuitry operable to change the operating characteristic of the sonic energy signal generator based on an output of the model processor.

9. The ultrasonic testing system of claim 1, the system further comprising:
the sonic energy signal generator having a property; and
the model processor deriving the operating characteristic from the property of the sonic energy signal generator.

10. The ultrasonic testing system of claim 1 wherein the sonic energy signal generator is a laser generator.

11. The ultrasonic testing system of claim 10 wherein the set of operational characteristic(s) associated with the sonic energy signal generator comprise at least one operational characteristic selected from a group consisting of optical wavelength, beam shape, beam size, pulse temporal profile, power, and time delay between successive pulses.

12. The ultrasonic testing system of claim 10 wherein the laser generator is selected from a group consisting of a ruby laser, $CO_2$ laser, Nd:YAG laser, Yb:YAG laser, Nd:YVO$_4$ laser, Nd:YLF laser, Tm:YLF laser, Ho:YLF laser, Ho:YAG laser, alexandrite laser, excimer laser, and titanium sapphire laser.

13. The ultrasonic testing system of claim 9 wherein the optical wavelength of the laser generator is obtained using a device selected from a group consisting of an optical parametric oscillator, an optical parametric amplifier, a Raman cell, a Brillouin cell, a difference frequency mixing setup, a sum frequency mixing setup, a harmonic generation setup, and a combination of an optical parametric oscillator and a difference frequency mixing setup.

14. The ultrasonic testing system of claim 1 wherein the sonic energy signal is an ultrasonic signal.

15. An ultrasonic testing system operable to test physical attribute(s) within a manufactured object, comprising:
a sonic energy signal generator operable to produce a sonic energy signal within the manufactured object, the sonic energy signal having properties determined by a set of operating characteristic(s) associated with the sonic energy generator;
a sonic energy detector operable to detect the sonic energy signal; a signal analyzer communicatively coupled to the sonic energy detector operable to extract information representative of the physical attribute(s) within the manufactured object from the sonic energy signal; and
a model processor, communicatively coupled to the signal analyzer and to the sonic energy signal generator, wherein the model processor is operable to:
determine when a favorable signal to noise ratio (SNR) is associated with the sonic energy signal;
determine an optimized set of operating characteristic(s) associated with the sonic energy generator, wherein the sonic energy signal, when using the optimized set of operating characteristic(s), is operable to produce sonic energy signal(s) within the manufactured object having an improved signal to noise ratio (SNR) when a favorable SNR is not associated with the sonic energy signal.

16. The ultrasonic testing system of claim 15 wherein the model processor selectively changes the set of operating characteristic(s) associated with the sonic energy generator.

17. The ultrasonic testing system of claim 15 wherein the ultrasonic testing system is operable to initiate a retest of a portion of the manufactured object when a favorable signal to noise ratio (SNR) is not associated with the sonic energy signal, wherein the retest utilizes the optimized set of a set of operating characteristic(s).

18. The ultrasonic testing system of claim 15 wherein the ultrasonic testing system tests sections of a portion of the manufactured object an order until the entire portion has been tested.

19. The ultrasonic testing system of claim 15 wherein information associated with the optimized set of operating characteristic(s) associated with the sonic energy generator a testing particular object is stored on a machine readable medium.

20. The ultrasonic testing system of claim 15, the system further comprising:
a representation of the manufactured object communicatively coupled to the model processor; and
the model processor deriving the operating state from the representation of the manufactured object.

21. The ultrasonic testing system of claim 20 wherein the representation of the manufactured object is a CAD model.

22. The ultrasonic testing system of claim 15 wherein the model processor derives the optimized set of operating characteristic(s) associated with the sonic energy generator before the sonic energy signal generator generates the sonic energy signal.

23. The ultrasonic testing system of claim 15, the system further comprising:
the model processor determines the optimized set of operating characteristic(s) associated with the sonic energy generator.

24. The ultrasonic testing system of claim 15, the model processor comprising:
a programmable circuitry;
the model processor deriving the operating state using the programmable circuitry.

25. The ultrasonic testing system of claim 15 wherein the sonic energy signal generator and sonic energy detector are found in a laser ultrasound system.

26. A method for generating an optimized sonic energy signal in a manufactured object that results in an improved signal to noise ratio (SNR) within sampled sonic energy signal(s), the method comprising:
deriving an optimized operating characteristic of a sonic energy signal generator;
adjusting the sonic energy signal generator to the optimized operating characteristic to produce the optimized sonic energy signal; and
operating the sonic energy signal generator to produce the optimized sonic energy signal.

27. A method for generating an improved sonic energy signal for use in testing a physical attribute of a manufactured object, the method comprising:
operating a sonic energy signal generator in a first state to produce a sonic energy signal about the manufactured object;
measuring the sonic energy signal with a sonic energy signal measuring device;
analyzing the result of the step of measuring;
determining when a favorable signal to noise ratio (SNR) is associated with the sonic energy signal;
deriving a second state of operation of the sonic energy signal generator based on the step of analyzing when a favorable SNR is not associated with the sonic energy signal, wherein the second state of operation is operable to produce sonic energy signal(s) within the manufactured object having an improved signal to noise ratio (SNR); and
selectively adjusting the sonic energy signal generator to operate in the second state to produce a second sonic energy signal.

28. The method of claim 27 wherein the step of analyzing is performed with a signal analyzer.

29. The method of claim 27 wherein the step of deriving is performed with a model processor.

30. The method of claim 27 wherein the second sonic energy signal is an optimized sonic energy signal.

31. The method of claim 27, wherein the step of deriving the second state uses a representation of the manufactured object.

32. The method of claim 31 wherein the representation of the manufactured object is a CAD model of the manufactured object.

33. The method of claim 27, the method further comprising:
the sonic energy signal generator having a property; and
the model processor deriving the second state of operation of the sonic energy signal generator from the property of the sonic energy signal generator.

34. The method of claim 27 wherein the sonic energy signal generator is a laser.

35. The method of claim 34 wherein the laser generator has at least one operational characteristic selected from a group consisting of optical wavelength, beam shape, beam size, pulse temporal profile, power, and time delay between successive pulses.

36. The method of claim 34 wherein said laser generator is selected from a group consisting of a ruby laser, $CO_2$ laser, Nd:YAG laser, Yb:YAG laser, Nd:YVO$_4$ laser, Nd:YLF laser, Tm:YLF laser, Ho:YLF laser, Ho:YAG laser, alexandrite laser, excimer laser, and titanium sapphire laser.

37. The method of claim 34 wherein the optical wavelength of the laser generator is obtained using a device selected from a group consisting of an optical parametric oscillator, an optical parametric amplifier, a Raman cell, a Brillouin cell, a difference frequency mixing setup, a sum frequency mixing setup, a harmonic generation setup, and a combination of an optical parametric oscillator and a difference frequency mixing setup.

38. The method of claim 27 wherein the sonic energy signal is an ultrasound signal.

39. The method claim 27 wherein the sonic energy signal measuring device comprises an interferometer selected from a group consisting of a confocal Fabry-Perot interferometer, a photorefractive two-wave mixing interferometer, a Michelson interferometer, a Mach-Zender interferometer, and a Sagnac interferometer.

40. A method for adaptively generating an improved sonic energy signal for use in testing a physical attribute of a manufactured object with a sonic signal generator and a sonic measuring device, the sonic signal generator operable in a first and a second state of operation, the sonic signal generator generating sonic signals about the manufactured object, the sonic measuring device measuring the sonic signals generated by the sonic signal generating device, the method comprising:
producing a first sonic energy signal with the sonic signal generating device operating in the first state of operation;
determining when a favorable signal to noise ratio (SNR) is associated with the sonic energy signal;
determining when a favorable signal to noise ratio (SNR) is not associated with the sonic energy signal, wherein a second state of operation is operable to produce sonic energy signal(s) within the manufactured object having an improved SNR;
selectively, based on the output of the step of determining:
deriving the second state of operation of the sonic generating device; and
producing a second sonic energy signal with the sonic signal generating device operating in the second state of operation.

41. The method of claim 40 wherein the step of selectively producing the second sonic energy signal comprises:
deriving the second state of operation of the sonic signal generating device using a model processor;
the model processor communicatively coupled to the sonic signal generating device;
the model processor deriving the second state of operation of the sonic signal generating device from the output of a signal analyzer, the signal analyzer communicatively coupled to the sonic measuring device;
adjusting the sonic signal generating device to the second state of operation;
producing the second sonic energy signal using the sonic signal generating device; and the sonic signal generating device producing the second sonic energy signal using the second state of operation.

42. The method of claim 40 wherein the model processor derives the second state of operation of the sonic signal generating device from a representation of the manufactured object.

43. The method of claim 42 wherein the representation of the manufactured object is a CAD model.

44. The method of claim 40 wherein the model processor derives the second state of operation of the sonic signal generating device from a property of the sonic signal generating device.

45. The method of claim 40 wherein the sonic signal generating device is a laser generator.

46. The method of claim 45 wherein the laser generator has at least one operational characteristic selected from a group consisting of optical wavelength, beam shape, beam size, pulse temporal profile, power, and time delay between successive pulses.

47. The method of claim 45 wherein said laser generator is selected from a group consisting of a ruby laser, $CO_2$ laser, Nd:YAG laser, Yb:YAG laser, Nd:YVO$_4$ laser, Nd:YLF laser, Tm:YLF laser, Ho:YLF laser, Ho:YAG laser, alexandrite laser, excimer laser, and titanium sapphire laser.

48. The method of claim 45 wherein the optical wavelength of the laser generator is obtained using a device selected from a group consisting of an optical parametric oscillator, an optical parametric amplifier, a Raman cell, a Brillouin cell, a difference frequency mixing setup, a sum frequency mixing setup, a harmonic generation setup, and a combination of an optical parametric oscillator and a difference frequency mixing setup.

49. The method of claim 40 wherein the sonic energy signal is an ultrasound signal.

50. The method claim 40 wherein the sonic energy signal measuring device comprises an interferometer selected from a group consisting of a confocal Fabry-Perot interferometer, a photorefractive two-wave mixing interferometer, a Michelson interferometer, a Mach-Zender interferometer, and a Sagnac interferometer.

51. The method of claim 40 wherein the testing of the physical attribute of the manufactured object is performed on a plurality of sections in an area of a manufactured object, the plurality of sections overlapping to form the area, the testing continuing until all of the sections have been tested.

52. The method of claim 51, the method further comprising:
    deriving a state of operation of the sonic signal generating device before testing each section.

53. A method for testing a physical characteristic in a portion of a manufactured object, the portion comprising sections, the method comprising:
    testing a first section in the portion of the manufactured object, the step of testing comprising:
        determining the initial operating state of a sonic energy signal generator, a model processor determining the initial operating state;
        operating the sonic energy signal generator in the initial operating state, the sonic energy signal generator initiating a sonic energy signal about the manufactured object,
        determining when a favorable signal to noise ratio (SNR) is not associated with the sonic energy signal, wherein a second state of operation is operable to produce sonic energy signal(s) within the manufactured object having an improved SNR; and another
    selectively operating in the other operating state based on the step of determining if another operating state is justified; and
    testing each of the remaining sections according to the step of testing the first section, until the portion has been completely tested.

54. A system for adaptively generating an improved sonic energy signal on or in a manufactured object using a sonic energy signal generator and a sonic energy signal measuring device, the sonic energy signal measuring device communicatively coupled to the sonic energy signal generator, measuring a sonic energy signal associated with the manufactured object, and producing a measured signal, the system comprising:
    a model processor communicatively coupled to the sonic energy signal generator, the model processor receiving the measured signal; and
    the model processor determining a new operating characteristic of the sonic energy signal generator from the measured signal when a favorable signal to noise ratio (SNR) is not associated with the sonic energy signal.

55. A method for adaptively generating a sonic energy signal for use in testing a manufactured object, the sonic energy signal produced about the manufactured object with a sonic energy signal generator operating in a first or a second mode of operation, the method comprising:
    determining when a favorable signal to noise ratio (SNR) is associated with the sonic energy signal operating in the first mode of operation, can be improved; and
    selectively enabling the sonic energy signal generator to be operated in the second mode of operation, based on the step of determining, such that the sonic energy signal generator is operable in the second state of operation to generate another sonic signal about the manufactured object.

* * * * *